US012594016B2

(12) United States Patent
Wang et al.

(10) Patent No.: US 12,594,016 B2
(45) Date of Patent: Apr. 7, 2026

(54) CONDUCTIVE ELECTRODE

(71) Applicant: Microsoft Technology Licensing, LLC, Redmond, WA (US)

(72) Inventors: Yu-Te Wang, Redmond, WA (US); Ivan Jelev Tashev, Kirkland, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 453 days.

(21) Appl. No.: 18/108,537

(22) Filed: Feb. 10, 2023

(65) Prior Publication Data

US 2024/0268741 A1 Aug. 15, 2024

(51) Int. Cl.
A61B 5/266 (2021.01)
A42B 1/017 (2021.01)

(52) U.S. Cl.
CPC .............. A61B 5/266 (2021.01); A42B 1/017 (2021.01); *A61B 2562/224* (2013.01)

(58) Field of Classification Search
CPC ...... A61B 5/266; A61B 2562/224; A42B 1/07
See application file for complete search history.

(56) References Cited

U.S. PATENT DOCUMENTS

| | | | | |
|---|---|---|---|---|
| 8,103,328 | B2 | 1/2012 | Turner | |
| 9,622,703 | B2 | 4/2017 | Badower | |
| 9,814,426 | B2 | 11/2017 | Connor | |
| 10,433,756 | B1 * | 10/2019 | Bachelder | A61B 5/6814 |
| 11,093,033 | B1 | 8/2021 | Wang et al. | |

| | | | |
|---|---|---|---|
| 2007/0255127 | A1 | 11/2007 | Mintz |
| 2008/0154112 | A1 | 6/2008 | Murphy |
| 2011/0074396 | A1 | 3/2011 | Liao |
| 2012/0179062 | A1 | 7/2012 | Wilson |
| 2013/0127708 | A1 | 5/2013 | Jung et al. |
| 2016/0063874 | A1 | 3/2016 | Tashev et al. |
| 2016/0081577 | A1 | 3/2016 | Sridhar |
| 2016/0143554 | A1 | 5/2016 | Lim |
| 2017/0281036 | A1 * | 10/2017 | Parvizi ................... A61B 5/325 |
| 2018/0263523 | A1 | 9/2018 | Puttilli |
| 2018/0271416 | A1 | 9/2018 | Begtrup |
| 2019/0192030 | A1 | 6/2019 | Watson |
| 2019/0192078 | A1 | 6/2019 | Sargent |
| 2019/0231235 | A1 | 8/2019 | Jeong |
| 2020/0107741 | A1 | 4/2020 | Fruitwala |

(Continued)

FOREIGN PATENT DOCUMENTS

| | | | |
|---|---|---|---|
| CN | 111281380 A | | 6/2020 |
| JP | 2005161025 A | * | 6/2005 |

(Continued)

OTHER PUBLICATIONS

International Search Report and Written Opinion received for PCT Application No. PCT/US2024/013905, May 6, 2024, 15 pages.

(Continued)

*Primary Examiner* — Linda C Dvorak
*Assistant Examiner* — Abigail Bock
(74) *Attorney, Agent, or Firm* — Rainier Patents, P.S.

(57) ABSTRACT

The description relates to self-dispensing electrodes. One example can include a curved hollow tube configured to hold a flowable conductive material and a selective retention mechanism positioned on the curved hollow tube and configured to retain the flowable conductive material in the hollow tube unless a force is imparted on the curved hollow tube.

20 Claims, 15 Drawing Sheets

SYSTEM 100C

ELECTROLYTIC FLUID 116
CURVED HOLLOW TUBE 202
SELECTIVE RETENTION MECHANISM 210
BALL 304
SELF-DISPENSING ELECTRODE 114
SECOND END 206
SOCKET 306
HOLE 302
SKIN 106
D1 D2 D3
z x y

(56)                    References Cited

U.S. PATENT DOCUMENTS

| | | |
|---|---|---|
| 2021/0240264 A1 | 8/2021 | Wilson et al. |
| 2023/0190175 A1 | 6/2023 | Wang |
| 2023/0190196 A1 | 6/2023 | Wang |

FOREIGN PATENT DOCUMENTS

| | | | |
|---|---|---|---|
| WO | 2012153263 A1 | 11/2012 |
| WO | 2015196554 A1 | 12/2015 |

OTHER PUBLICATIONS

Final Office Action mailed on Jan. 7, 2025, in U.S. Appl. No. 17/555,311, 16 pages.
Final Office Action mailed on Jun. 25, 2025, in U.S. Appl. No. 17/555,278, 24 pages.
International Preliminary Report on Patentability received for PCT Application No. PCT/US2024/013905, mailed on Aug. 21, 2025, 10 pages.
Non-Final Office Action mailed on Aug. 8, 2025, in U.S. Appl. No. 17/555,278, 24 pages.
Non-Final Office Action mailed on Jan. 13, 2025, in U.S. Appl. No. 17/555,278, 17 pages.
Non-Final Office Action mailed on Sep. 6, 2024, in U.S. Appl. No. 17/555,311, 17 pages.

* cited by examiner

SYSTEM 100A

SYSTEM 100A

WEARABLE COMPONENT 112

DEVICE 110

WIRE 120(1)
WIRE 120(2)
WIRE 120(3)

114(1)
116
116
114(3)

SKIN 106

114(2)

ELEC
COMP
122
124

HEAD 104

USER 102

SYSTEM 100A

SYSTEM 100A

SYSTEM 100A

SYSTEM 100D

SYSTEM 100D

SYSTEM 100E

SYSTEM 100E

SYSTEM 100F

SYSTEM 100F

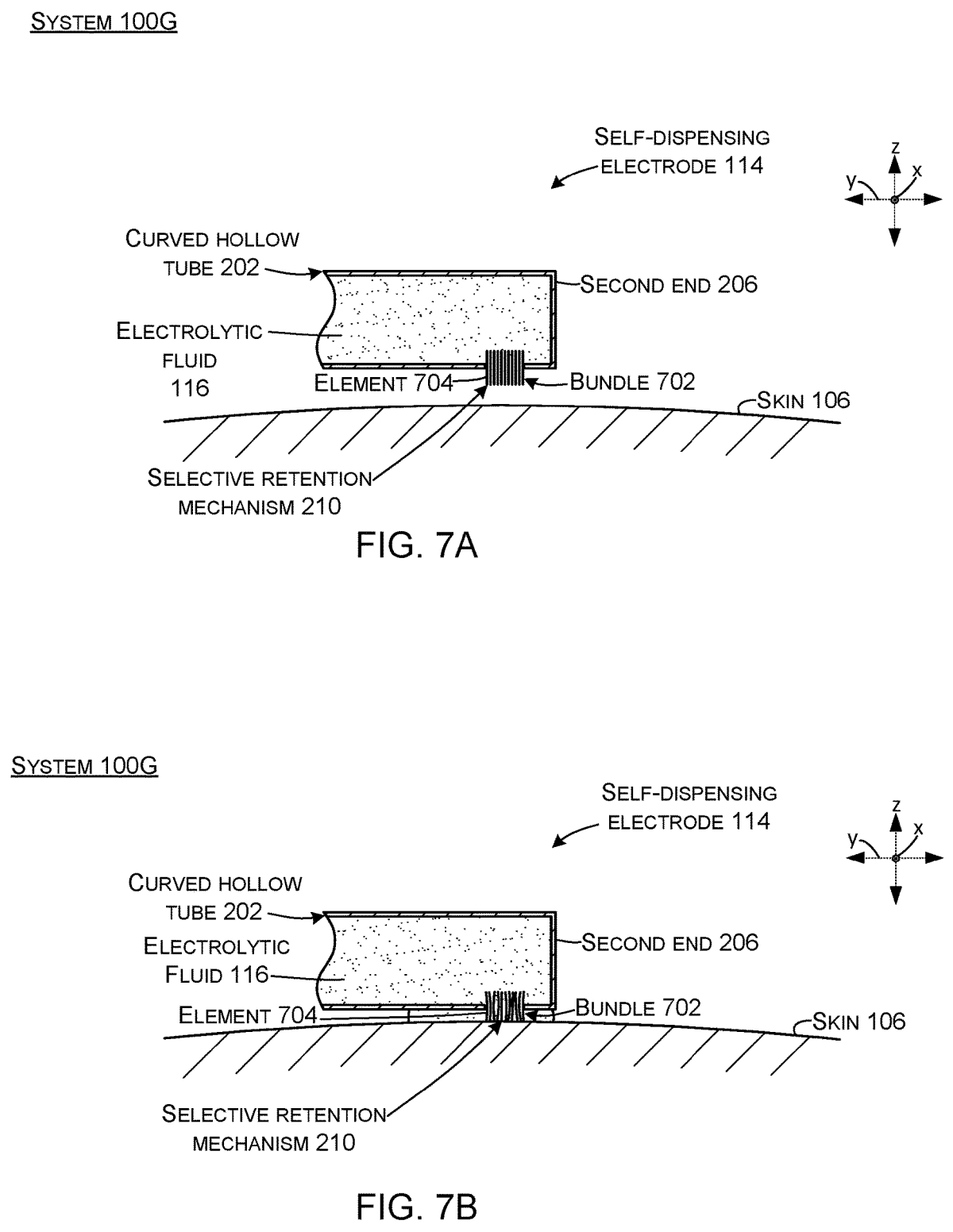

SYSTEM 100G

SELF-DISPENSING
ELECTRODE 114

CURVED HOLLOW
TUBE 202

SECOND END 206

ELECTROLYTIC
FLUID
116

ELEMENT 704          BUNDLE 702

SKIN 106

SELECTIVE RETENTION
MECHANISM 210

FIG. 7A

SYSTEM 100G

SELF-DISPENSING
ELECTRODE 114

CURVED HOLLOW
TUBE 202

ELECTROLYTIC
FLUID 116

SECOND END 206

ELEMENT 704          BUNDLE 702

SKIN 106

SELECTIVE RETENTION
MECHANISM 210

FIG. 7B

SYSTEM 100I

SYSTEM 100I

SYSTEM 100K

CONDUCTIVE ELECTRODE

BACKGROUND

Electrodes are positioned on humans and other animals to sense electrical signals associated with various biological processes, such as heart function and/or brain function.

SUMMARY

This patent relates to self-dispensing electrodes. One example can include a curved hollow tube configured to hold a flowable conductive material and a selective retention mechanism positioned on the curved hollow tube and configured to retain the flowable conductive material in the hollow tube unless a force is imparted on the curved hollow tube.

Another example can entail a wearable component configured to be positioned relative to a body part of a user and an electrode associated with the wearable component and configured to engage the user's body part. The electrode can include a curved hollow tube configured to retain a flowable conductive material unless a force is exerted on the electrode toward the wearable component.

These examples are intended to provide a summary of some of the described concepts and are not intended to be inclusive or limiting.

BRIEF DESCRIPTION OF THE DRAWINGS

The accompanying drawings illustrate implementations of the concepts conveyed in the present document. Features of the illustrated implementations can be more readily understood by reference to the following description taken in conjunction with the accompanying drawings. Like reference numbers in the various drawings are used wherever feasible to indicate like elements. Further, the left-most numeral of each reference number conveys the figure and associated discussion where the reference number is first introduced. Where space permits, elements and their associated reference numbers are both shown on the drawing page for the reader's convenience. Otherwise, only the reference numbers are shown.

FIGS. 3A-3D, 4A, 4B, 5A, 5B, 6A, 6B, 7A, 7B, 8A, and 8B show sectional views of example devices in accordance with some implementations of the present concepts.

DESCRIPTION

Figure 1A:
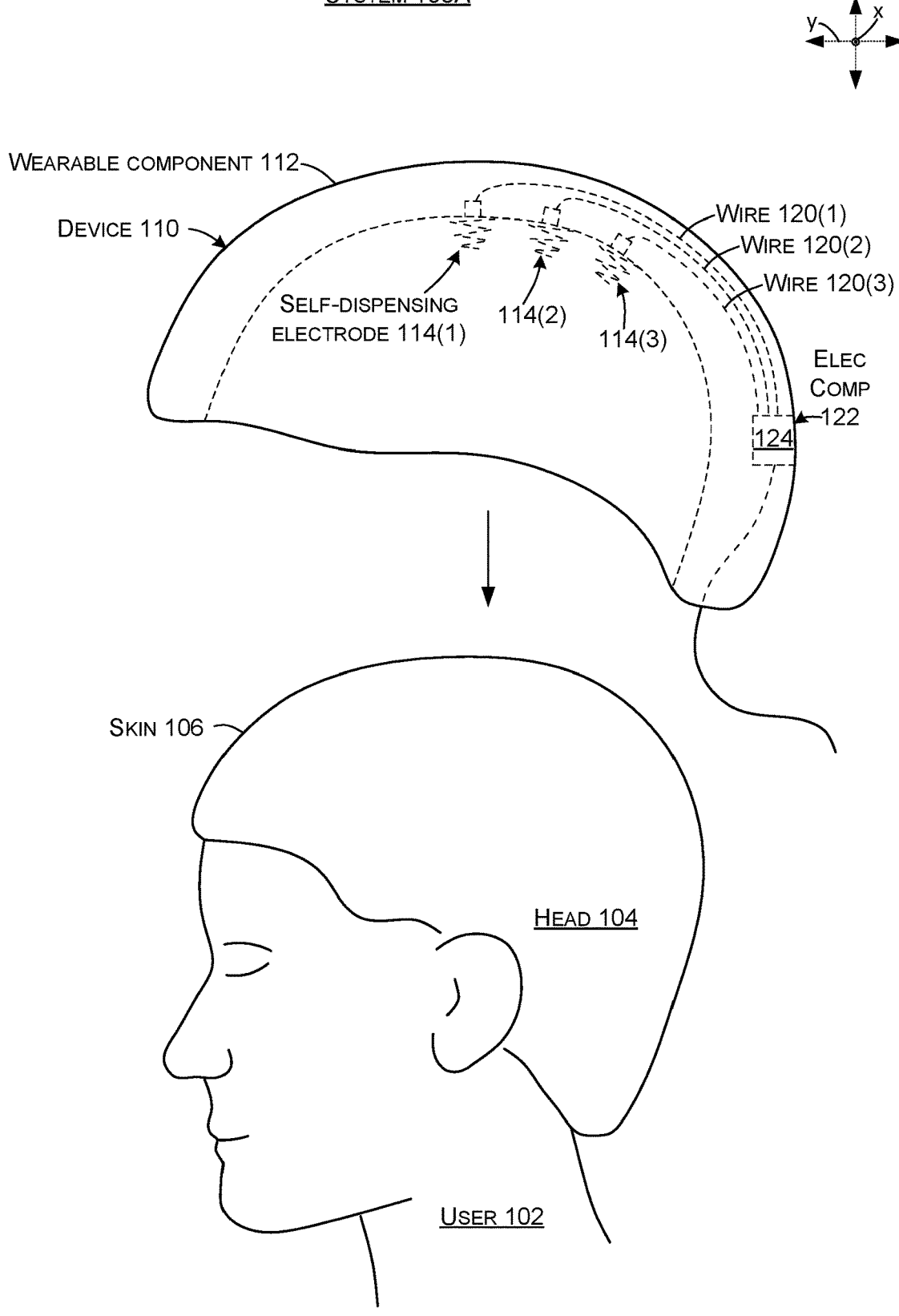
FIGS. 1A-1E, 10B, and 11 show elevational views of example devices in accordance with some implementations of the present concepts.

The present concepts relate to self-dispensing electrodes and devices employing self-dispensing electrodes to sense biological processes. Traditionally, a technician would dispense a flowable conductive material, such as a conductive liquid on the user's skin and align an electrode with the conductive liquid to reduce impedance associated with the user's skin. This technique required manual visual alignment of the electrode and the dispensed conductive liquid. Thus, for some electrode positions that are not visible to the user, such as on the back of the head, the user could not be trained to self-apply the electrodes and the technician was required for proper installation. Further, if the user wanted to temporarily take off the electrodes the whole process had to be repeated (e.g., the electrodes had to aligned with the conductive liquid).

The present inventive concepts provide technical solutions to these and other technical problems. The technical solutions involve curved hollow electrodes that store the conductive liquid and automatically dispense the conductive liquid when the electrodes contact the user's skin and stop dispensing when the contact ceases. Stated another way, contact with the user's skin creates a force on the curved hollow electrode that causes the dispensing. When the force ceases, the dispensing ceases. Thus, the curved hollow electrodes described herein can be viewed as 'self-dispensing electrodes.' The self-dispensing electrodes can be resilient (e.g., spring like) in nature. This aspect enhances the self-dispensing nature of the electrodes. Recall that contact with the user's skin creates a force on the self-dispensing electrode that effects dispensing. This force can also change the shape (e.g., bend) of the self-dispensing electrode. The shape change can provide desired functionalities. First, given the resilient nature of the self-dispensing electrode, the electrode creates an opposite force back toward the skin to maintain uniform contact between the electrode and the skin. This can be analogized to the way that springs in the suspension of a car help to maintain contact between the tire and uneven road surfaces. This aspect facilitates consistent skin to electrode contact as the user moves and/or muscles contract, etc. Second, the resilient nature of the self-dispensing electrode can limit force between the self-dispensing electrode and a small portion of the user's skin by bending (e.g., more force produces more bending). Third, the curved nature of the self-dispensing electrode increases its length and thus storage capacity comparted to a straight electrode of the same width/diameter. These and other facets are described in further detail below by way of example.

FIGS. 1A-1E collectively show an example system 100A in which the present concepts can be implemented. In this case, the system 100A relates to a human or animal user 102. The present concepts can allow sensing of a user's body parts, such as the head 104, whether the skin 106 is bare or hair covered. The system 100A includes a device 110 that entails a wearable component 112 and one or more self-dispensing electrodes 114. The self-dispensing electrodes 114 can hold a flowable conductive material, such as an electrolytic fluid 116 (e.g., conductive gel). In this example, the wearable component 112 can be manifest as a helmet, hat, visor, or band, among others. The self-dispensing electrodes 114 can be physically secured to the wearable component 112 and oriented toward the user (e.g., on the inside of the hat facing inward toward the user's head). The self-dispensing electrodes 114 can be electrically connected to conductive wires 120 which lead to an electronic component 122, such as an amplifier 124. Ultimately, the signals sensed by the self-dispensing electrodes 114 can be analyzed by a computing device. The computing device can be manifest as the electronic components 122 on the device 110. Alternatively or additionally, the computing device can be an external computing device (not shown) which receives wired or wireless signals from the device 110.

Figure 1B:
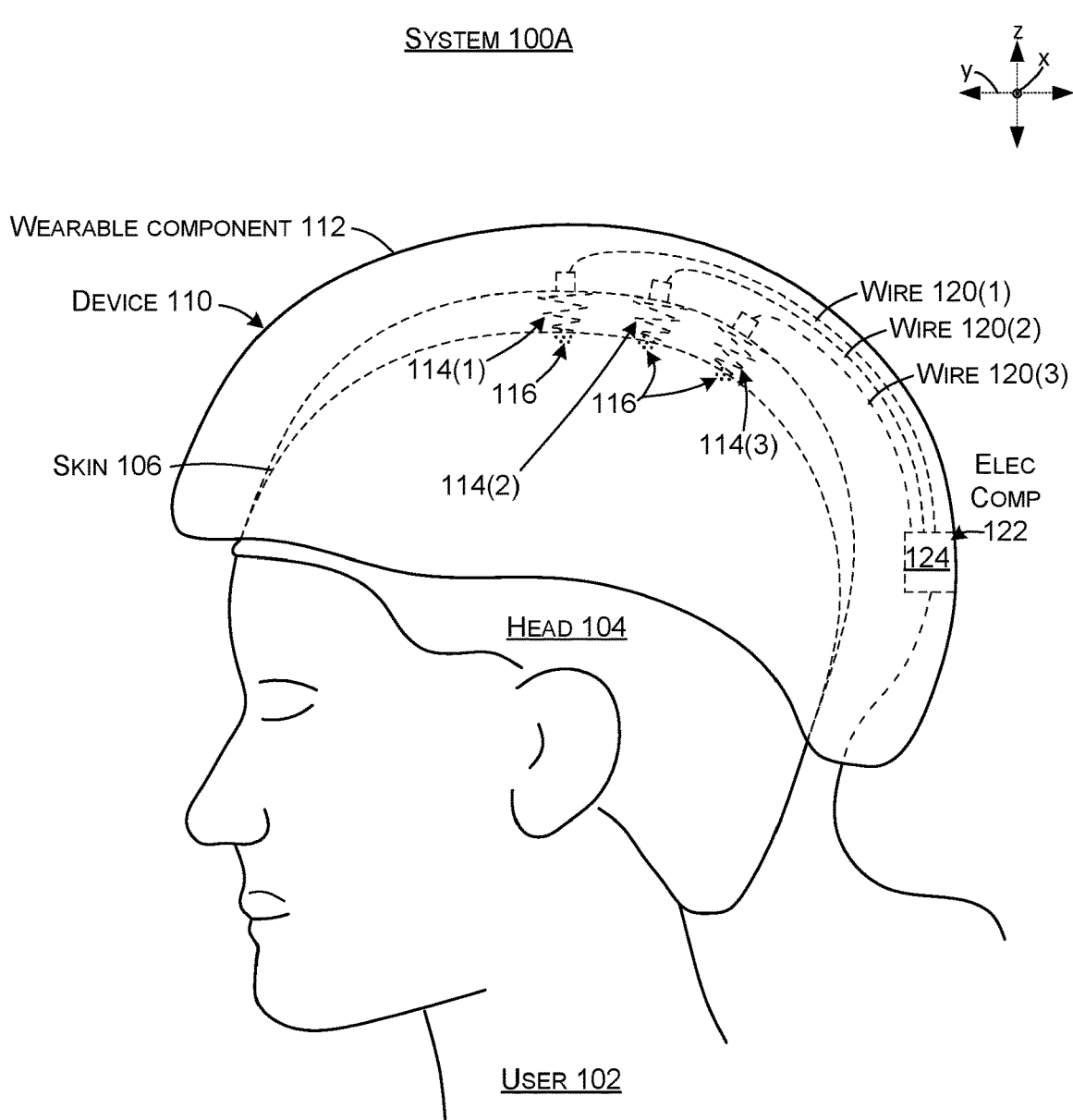

FIG. 1A shows the device 110 prior to being positioned on the user 102. FIG. 1B shows the device 110 positioned on the user's head. The self-dispensing electrodes 114 are contacting the user's skin 106. The user's skin 106 is creating a slight (upward) force on the self-dispensing electrodes 114. This upward force causes the self-dispensing electrodes 114 to release small amounts of electrolytic fluid 116. The electrolytic fluid on the skin creates a more efficient electrical path from the user to the self-dispensing electrodes 114. Note that with traditional techniques electrolytic fluid 116 was manually dispensed by a technician and then the electrode had to be manually aligned with the electrolytic fluid. In contrast, the present concepts offer a technical solution in that the electrolytic fluid 116 is dispensed from the end of the self-dispensing electrodes 114 where it contacts the skin and thus by definition the self-dispensing electrode 114 and the electrolytic fluid 116 it dispenses are automatically aligned.

Figure 1C:
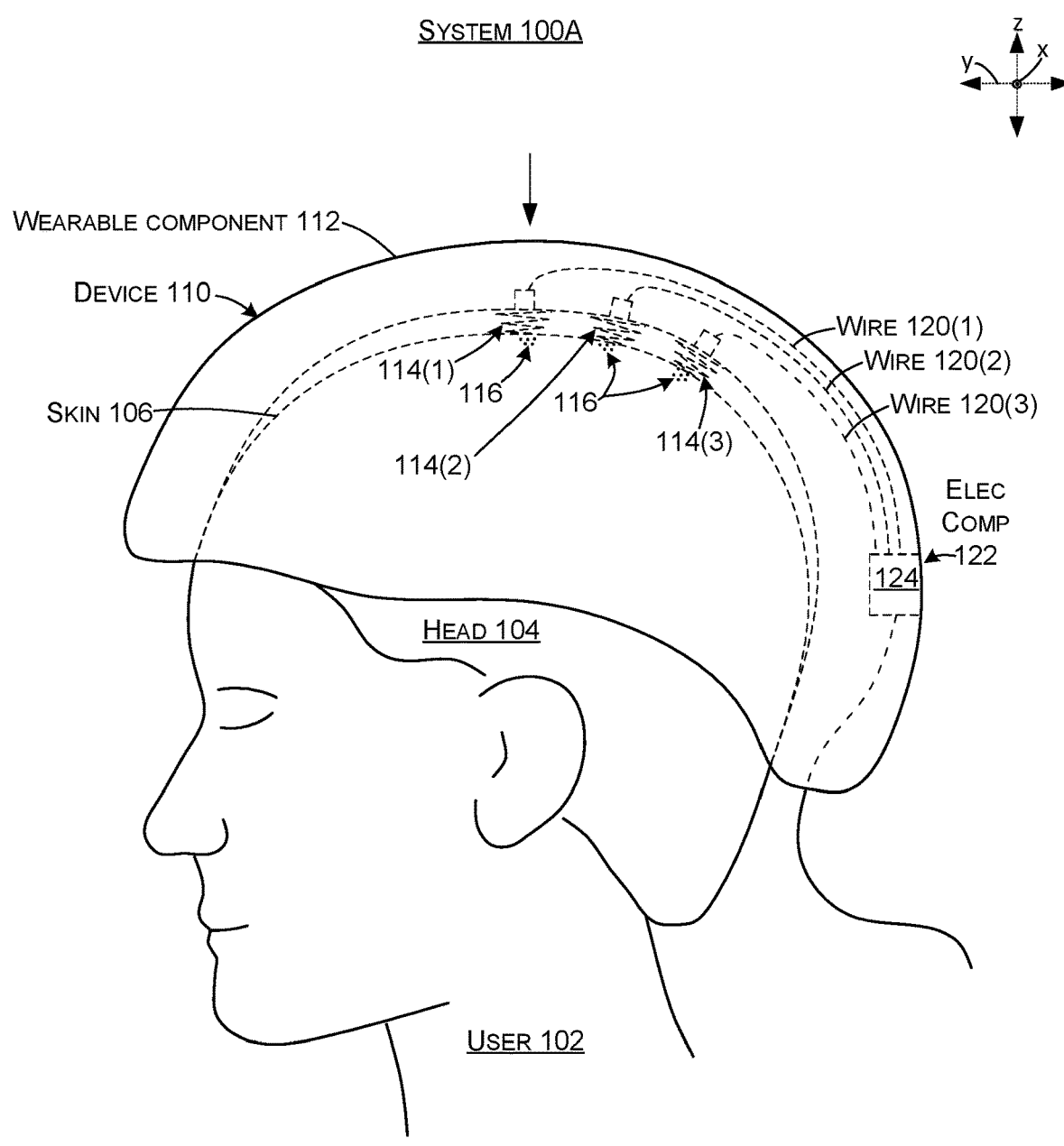

FIG. 1C is similar to FIG. 1B, but the device 110 is forced downward on the user's head. The user's body is generally rigid and thus creates a correspondingly larger upward force on the self-dispensing electrodes 114 (e.g., the self-dispensing electrodes 114 experience compressive forces between the user and the wearable component 112). As with FIG. 1B, this upward force causes electrolytic fluid 116 to be dispensed from the self-dispensing electrodes 114. Recall that the self-dispensing electrodes 114 are resilient in nature. The increased force causes the self-dispensing electrodes 114 to bend (e.g., in this case the bending decreases an overall length in the z reference direction). This bending reduces/eliminates risk of the self-dispensing electrodes 114 puncturing the user's skin as could occur with traditional rigid electrodes that can act in a spear-like manner when pushed against the user.

Figure 1D:
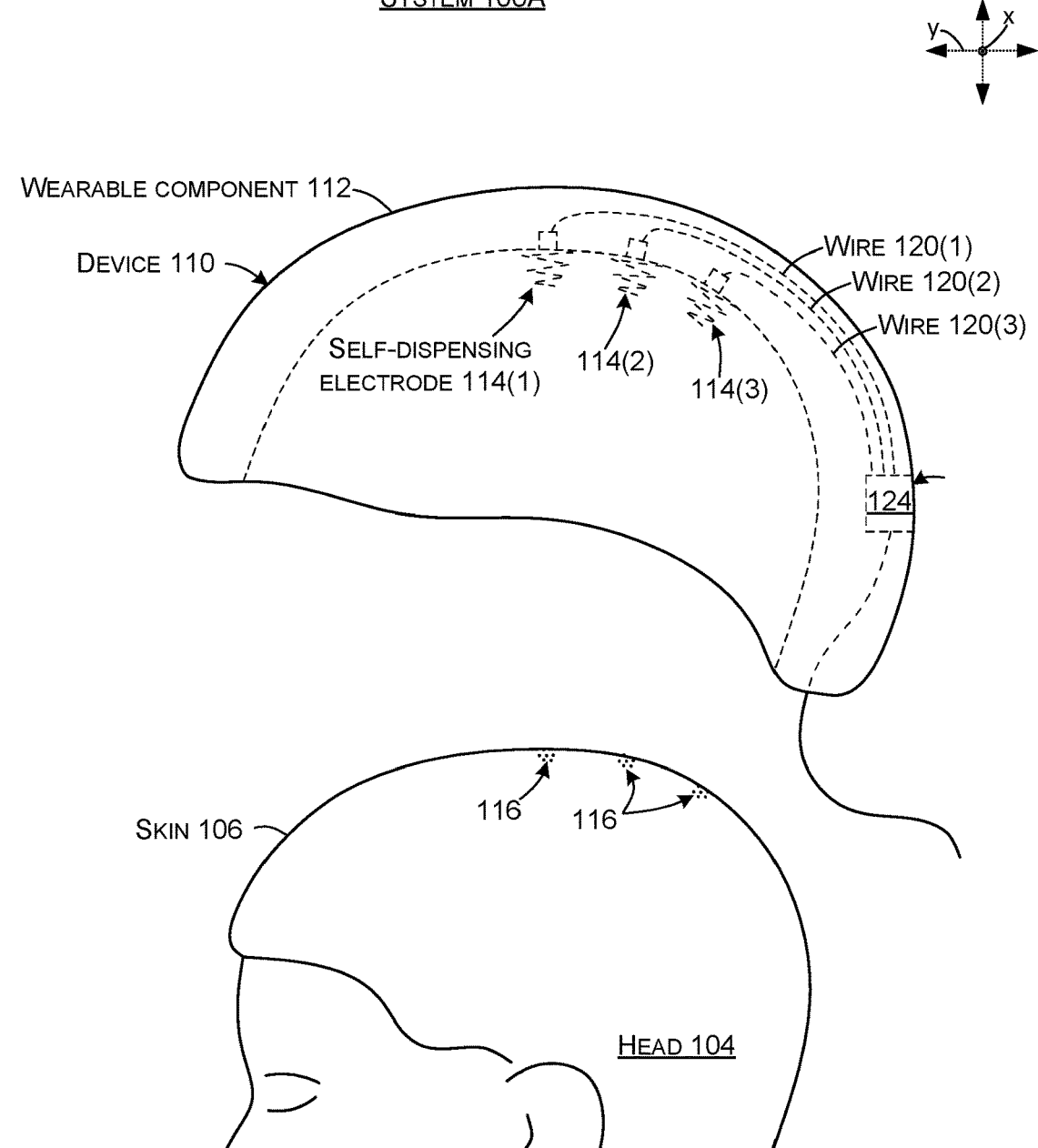

FIG. 1D shows the device 110 lifted off of the user's skin. At this point, contact forces cease and the self-dispensing electrodes 114 stop dispensing electrolytic fluid 116. Further, the resilient nature of the self-dispensing electrodes 114 causes them to return to their original dimensions (e.g., shape).

Figure 1E:
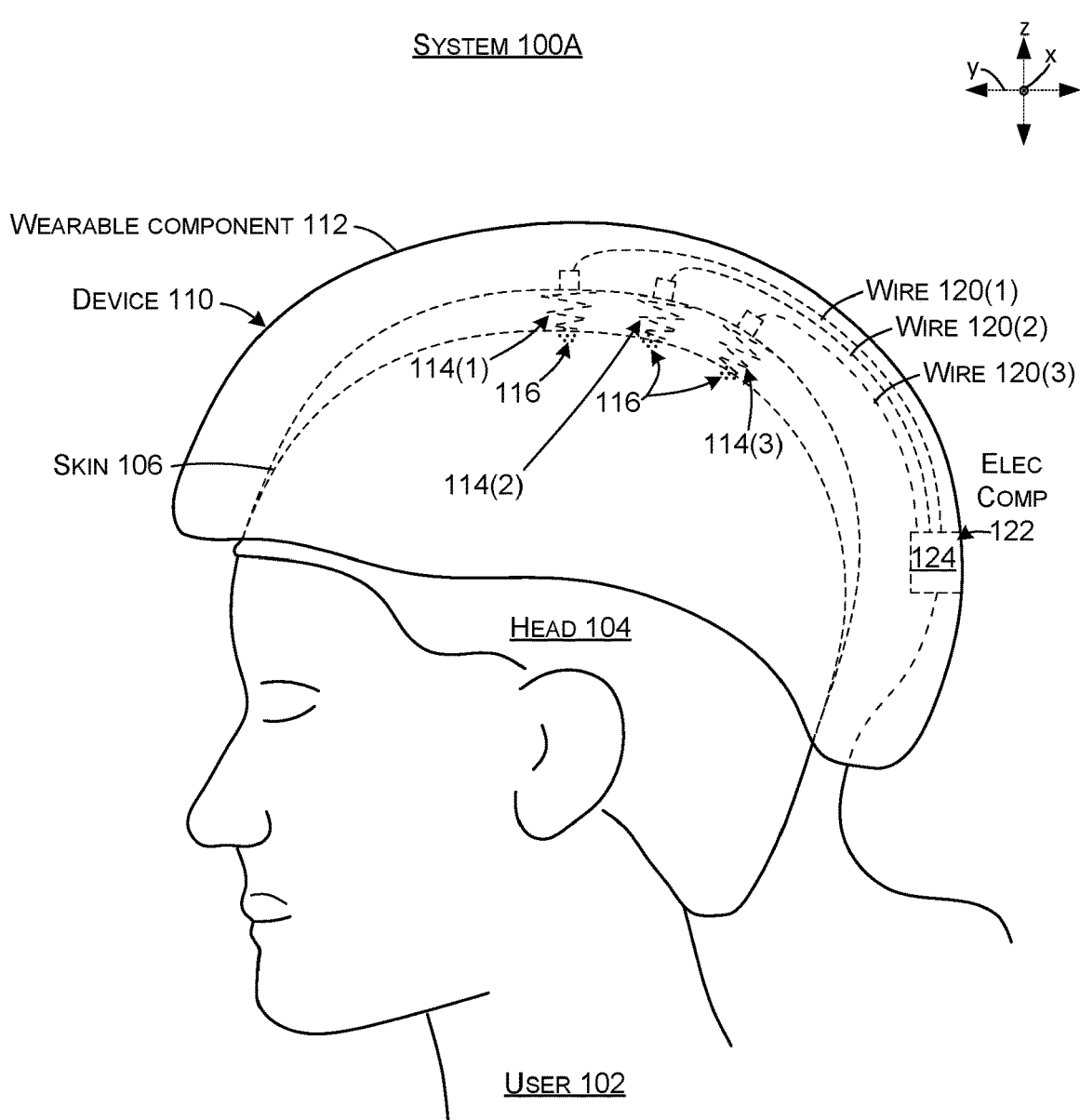

FIG. 1E shows the device 110 once again positioned against the user's skin 106. Upon contact, the self-dispensing electrodes 114 release more electrolytic fluid 116, which since it is dispensed from the self-dispensing electrodes 114 is by definition aligned with the electrode and no manual alignment is required. Further, the self-dispensing electrodes 114 release electrolytic fluid 116 proximate to the force created by the user's skin (e.g., at the skin level). This configuration results in more of the electrolytic fluid 116 actually contributing to the electrical conduction compared to traditional manual dispensing, which may tend to be misaligned and/or applied to the overlying hair rather than the skin.

Figures 2A, 2B:
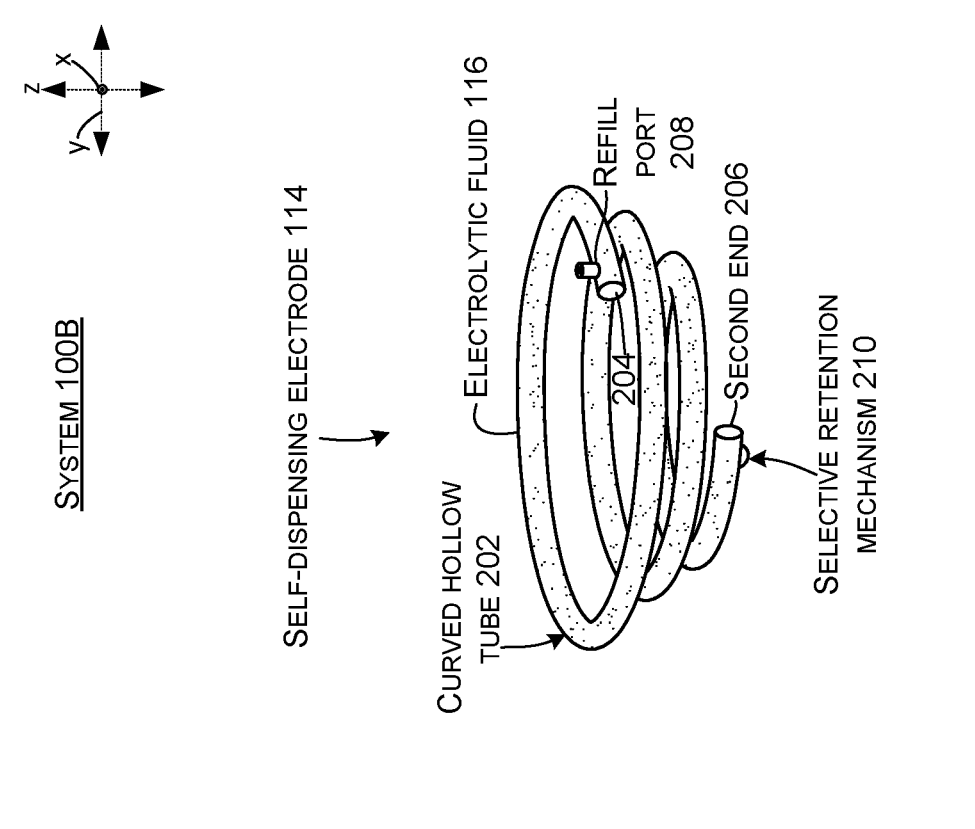
FIGS. 2A, 2B, 9A, 9B, and 10A show perspective views of example devices in accordance with some implementations of the present concepts.

FIGS. 2A and 2B collectively show details of system 100B that includes example deformable electrodes that are manifest as self-dispensing electrodes 114. (Note that the use of the letter suffix (e.g., 'A,' 'B,' 'C,' etc.) is intended to convey that different systems 100 can have different components and/or like components can be different between systems). FIG. 2A shows the self-dispensing electrode 114 in a relaxed, non-dispensing configuration and FIG. 2B shows the self-dispensing electrode 114 in a deformed (e.g., compressed) dispensing configuration.

In this case, the self-dispensing electrode 114 entails a curved hollow tube 202. The curved hollow tube 202 can be formed from an electrically insulative resilient material, such as various polymers. In other implementation, the curved hollow tube 202 can be electrically insulative on the outside surface and electrically conductive on the inside surface. For instance, the curved hollow tube 202 could be formed from an electrically insulative polymer and the inside surface could be coated with a conductor, such as silver/silver chloride. The curved hollow tube 202 has a first end 204 and an opposite second end 206. The first end 204 is positioned proximate to the wearable component 112 of FIGS. 1A-1E. The second end 206 is positioned distal from the wearable component and towards the user. In this case, the hollow tube 202 is curved into a spiral shape. Alternative shapes are described below relative to FIGS. 9A and 9B.

The curved hollow tube 202 can hold (e.g., act as a reservoir for) the electrolytic fluid 116. A refill port 208 is positioned proximate to the first end 204. The refill port 208 allows the hollow tube to be refilled with electrolytic fluid 116. A selective retention mechanism 210 is positioned on the hollow tube 202 at, or proximate to, the second end 206. The selective retention mechanism 210 controls whether electrolytic fluid 116 is released. Force (e.g., skin contact pressure) on the self-dispensing electrode 114 in the positive z reference direction can both cause the selective retention mechanism 210 to release electrolytic fluid 116 and change the shape of the curved hollow tube 202. When the force is removed, selective retention mechanism 210 stops releasing electrolytic fluid 116 and the resilient nature of the curved hollow tube 202 causes it to return to the original shape.

The self-dispensing electrode 114 can be implemented across a wide size range. For instance, the self-dispensing electrode 114 can have a width (in the y reference direction) of less than a centimeter to multiple centimeters. The self-dispensing electrode 114 can have a height (in the z reference direction) of less than a centimeter to multiple centimeters. In one such example implementation, the width is about 1.5 cm and the height is about 2 cm in the relaxed shape of FIG. 2A and about 0.5 cm in the compressed shape of FIG. 2B. In the illustrated configuration, the cross-sectional shape of the curved hollow tube 202 is circular. Other implementations can employ other shapes, such as rectangular shapes. The inside diameter/width of the curved hollow tube 202 can range from about 0.2 cm to about 0.5 cm, for example, in various implementations.

FIGS. 3A-8B show several example selective retention mechanisms 210 in more detail.

Figure 3A:
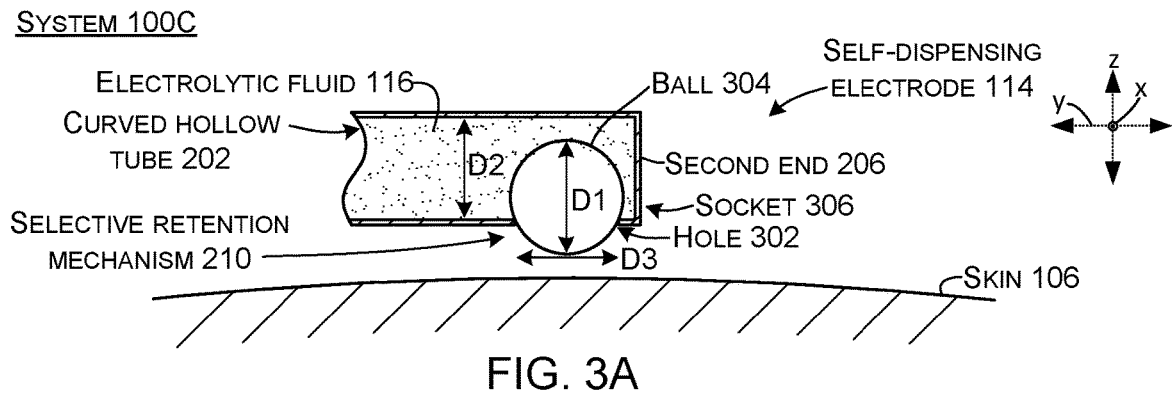

FIGS. 3A-3D relate to system 100C and show example selective retention mechanism 210 on example self-dispensing electrode 114. As indicated in FIG. 3A, selective retention mechanism 210 entails a hole 302 formed in curved hollow tube 202. A ball 304, such as a ball bearing, is positioned in the curved hollow tube aligned with the hole 302. The ball 304 has an outside diameter D1 that is larger than an inside diameter D2 of the curved hollow tube 202 and a diameter D3 of the hole 302. Thus, the ball 304 is captive at the hole 302 and cannot fall out of the hole 302 or move down the curved hollow tube 202. Thus, the curved hollow tube can be viewed as defining a socket 306 that holds the ball 304 captive.

In the orientation of FIG. 3A, the forces acting upon the ball 304 is gravity pulling the ball 304 downward (e.g., in the −z reference direction) against the hole 302 and the weight of the electrolytic fluid 116 in the curved hollow tube 202 pushing the ball downward (e.g., in the −z reference direction). The ball 304 forms a seal or seat in the hole 302 (e.g., with the curved hollow tube 202 surrounding the hole). This seal prevents electrolytic fluid 116 from being dispensed from the curved hollow tube 202 and can be viewed as a 'non-dispensing state' of the selective retention mechanism 210.

Figure 3B:
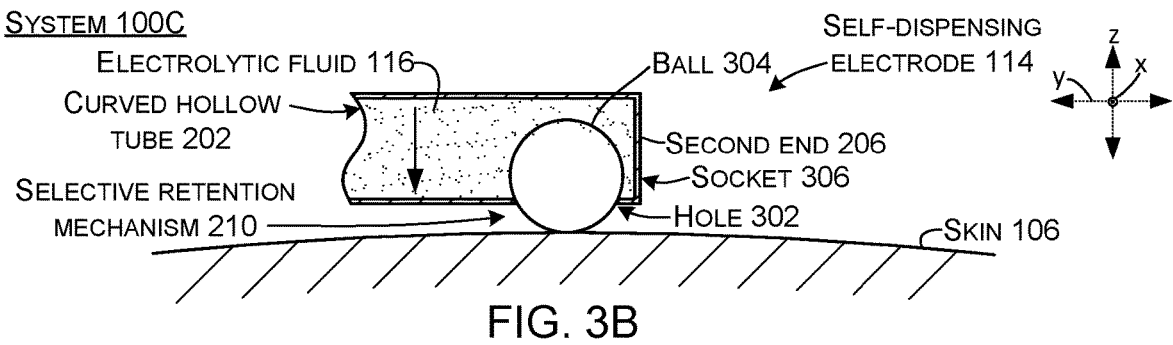

FIG. 3B shows the curved hollow tube lowered downward until the selective retention mechanism 210 (e.g., the ball 304) contacts the user's skin 106. The user's skin 106 creates an upward pressure or force on the ball 304.

Figure 3C:
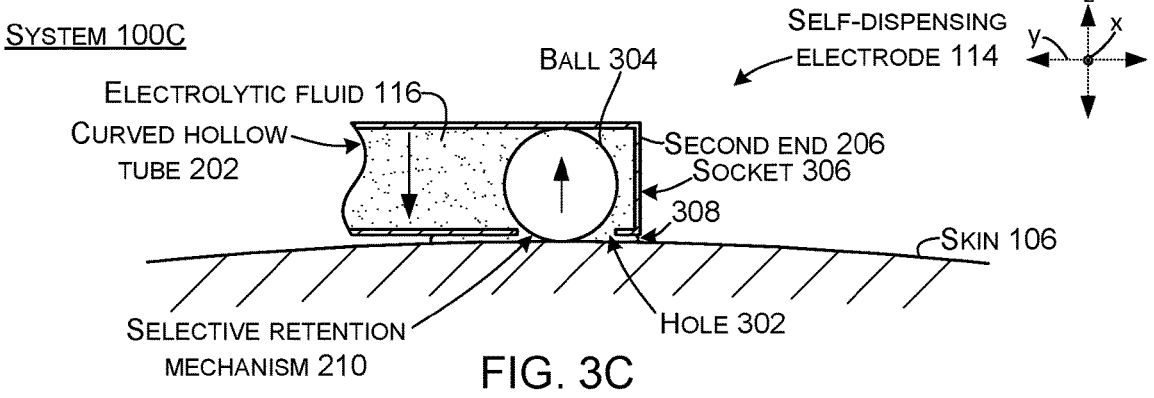

FIG. 3C shows the upward pressure or force on the ball 304 created by the user's skin 106 moving the ball slightly upwardly in the +Z reference direction. The upward movement of the ball 304 unseats the ball from the hole 302 and allows electrolytic fluid 116 to flow around the ball and out of the curved hollow tube (e.g., be dispensed from the selective retention mechanism 210) and onto the user's skin 106 as indicated at 308. The unseated ball 304 and associated electrolytic fluid 116 flow can be viewed as a 'dispensing state' of the selective retention mechanism 210. Alternatively or additionally to electrolytic fluid flowing between the ball 304 and the socket 306, rotation of the ball against the skin can dispense electrolytic fluid 116 to the skin 106 in a manner analogous to the functioning of a ball point pen.

Figure 3D:
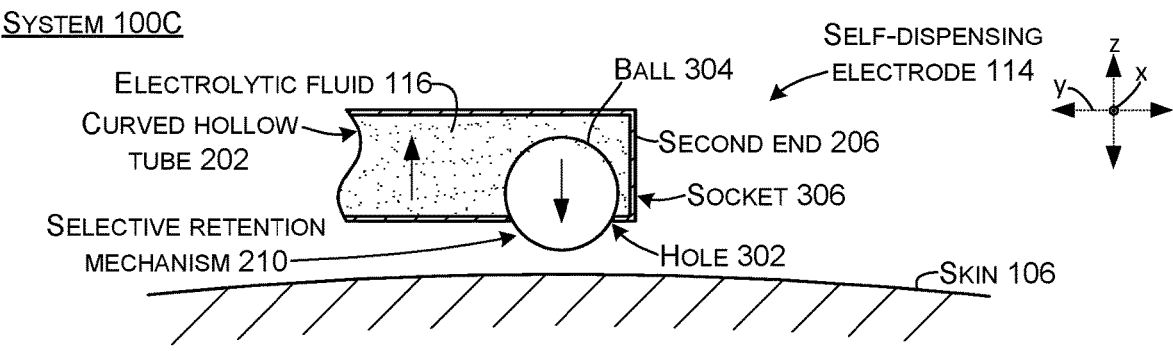

FIG. 3D shows the selective retention mechanism 210 lifted upward in the +z reference direction away from the user's skin 106. As contact between the ball 304 and the skin ceases, the ball moves downwardly in the −z reference direction and reseats in the hole 302. Thus, the selective retention mechanism 210 has returned to the 'non-dispensing state.'

In this implementation, the ball 304 is captive between the hole 302 and the upper inside surface of the curved hollow tube 202 and thus can be viewed as a ball 304 and socket 306 configuration. Two more ball and socket configurations are described below relative to FIGS. 4A-4B and 5A-5B. Note also, that movement of the ball 304 in the socket 306 can be different in different implementations. In this example, the ball 304 moves linearly in the socket 306 and electrolytic fluid flows between the ball and socket.

In other implementations, the position of the ball 304 may be relatively fixed in the socket 306, but the ball can rotate. In such a configuration, electrolytic fluid 116 coats the top of the ball 304 and as the ball contacts the skin 106 the ball is rotated as the ball moves linearly (e.g., in the x and/or y reference directions) slightly relative to the skin. This movement rotates the ball and moves the top of the ball to the bottom where the coated electrolytic fluid 116 contacts the skin. The ball 304 can be made out of, and/or coated with, a conductive material such as silver, gold, or copper, among others. Thus, the ball 304 and the dispensed electrolytic fluid 116 contribute to the conductive path of the self-dispensing electrode 114. The biological signals go through the tissue to the skin 106 and into the electrolytic fluid 116, through the electrolytic fluid 116 to the ball 304 and from the ball to electrolytic fluid 116 in the curved hollow tube 202 and to the first end (204, FIG. 2A) where it is conveyed into the wire (120, FIG. 1A). Alternatively, as mentioned above, the inside surface of the curved hollow tube can be conductive and contribute to the signal path.

Figure 4A:
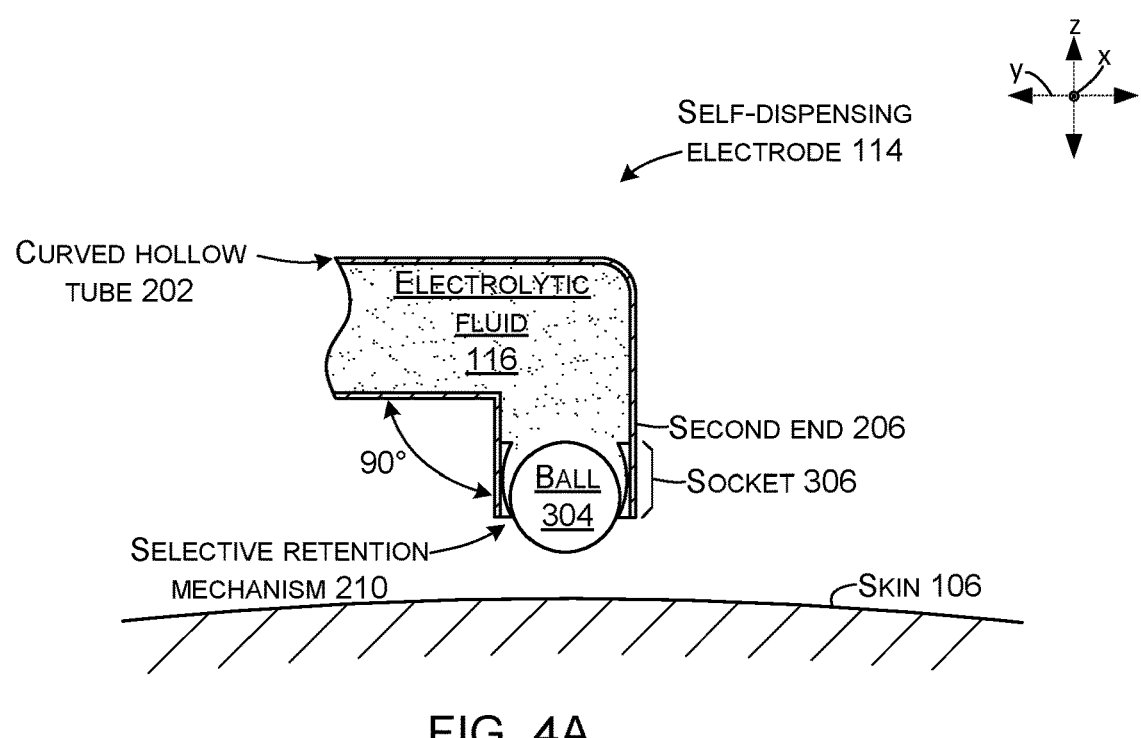
Figure 4B:
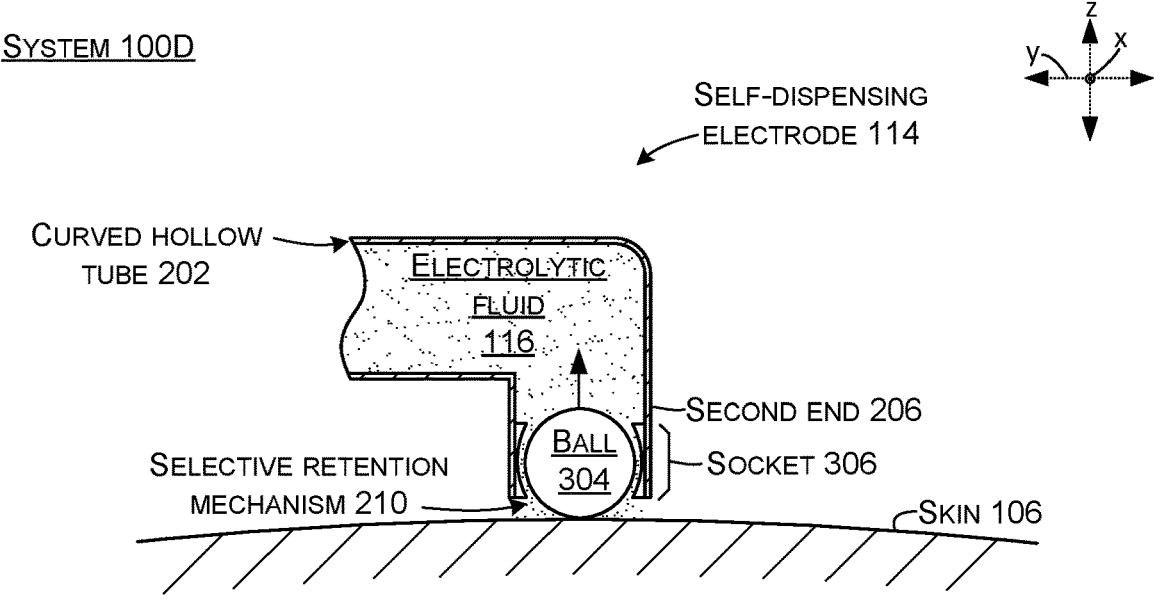

FIGS. 4A and 4B relate to system 100D and collectively show another example selective retention mechanism 210 employed on a self-dispensing electrode 114. In this case, the second end 206 of the curved hollow tube 202 is bent 90 degrees relative to a remainder of the tube. Ball 304 is captured in socket 306. When viewed along the z reference axis, the socket 306 has upper and lower diameters that are smaller than a diameter of the ball. Interposed between these upper and lower diameters is a region that has a diameter that is wider than the diameter of the ball. Thus, the ball 304 has a defined or limited range of movement between the upper and lower diameters of the socket, but the ball cannot pass out of the socket in the +z reference direction or the −z reference direction. Note that as mentioned above, the socket may allow the ball 304 to spin/rotate in the socket, but not to move linearly. The spinning can deliver electrolytic fluid from inside the curved hollow tube 202 to the user's skin 106.

FIG. 4A shows a non-dispensing or resting state where the ball 304 is positioned at the lower end of the socket 306 and is blocking electrolytic fluid 116 from exiting the curved hollow tube 202.

FIG. 4B shows contact with the user's skin 106 creating an upward force or pressure on the ball 304. The upward force has moved the ball 304 into an intermediate position in the socket 306 where electrolytic fluid 116 can flow between the ball 304 and the socket 306 and onto the user's skin proximate to the ball 304. The selective retention mechanism 210 is now in a dispensing state.

If the self-dispensing electrode 114 is moved away from the user and contact with the user ceases, gravity will pull the ball 304 back into the position in the socket 306 shown in FIG. 4A and the electrolytic fluid 116 flow will stop. In this implementation, gravity and pressure forces generated by contact with the user's skin control the position of the ball. Other implementations can create pressure within the curved hollow tube 202. For instance, a spring could act directly upon the ball 304 to bias the ball toward the position of FIG. 4A. A spring bias acting on the selective retention mechanism is described below relative to FIGS. 6A and 6B. Alternatively, a spring plunger could be employed to pressurize the inside of the curved hollow tube 202 including the electrolytic fluid 116 and indirectly the ball 304. Such a configuration could be employed in device configurations where the self-dispensing electrode 114 is oriented horizontally or upside down (e.g., second end 206 higher than first end 204).

Note that in some implementations the outside surface of the ball 304, the inside surface of the socket 306, and the inside surface of the curved hollow tube 202 can be coated with conductors, such as silver/silver chloride. Thus, the electrical path of the biological signals is from (or can include) the tissue to the skin, to the dispensed electrolytic fluid on the skin, to the ball, to the socket, to the inside of the curved hollow tube, and up the inside of the curved hollow tube to the wire 120 of FIG. 1A.

Figure 5A:
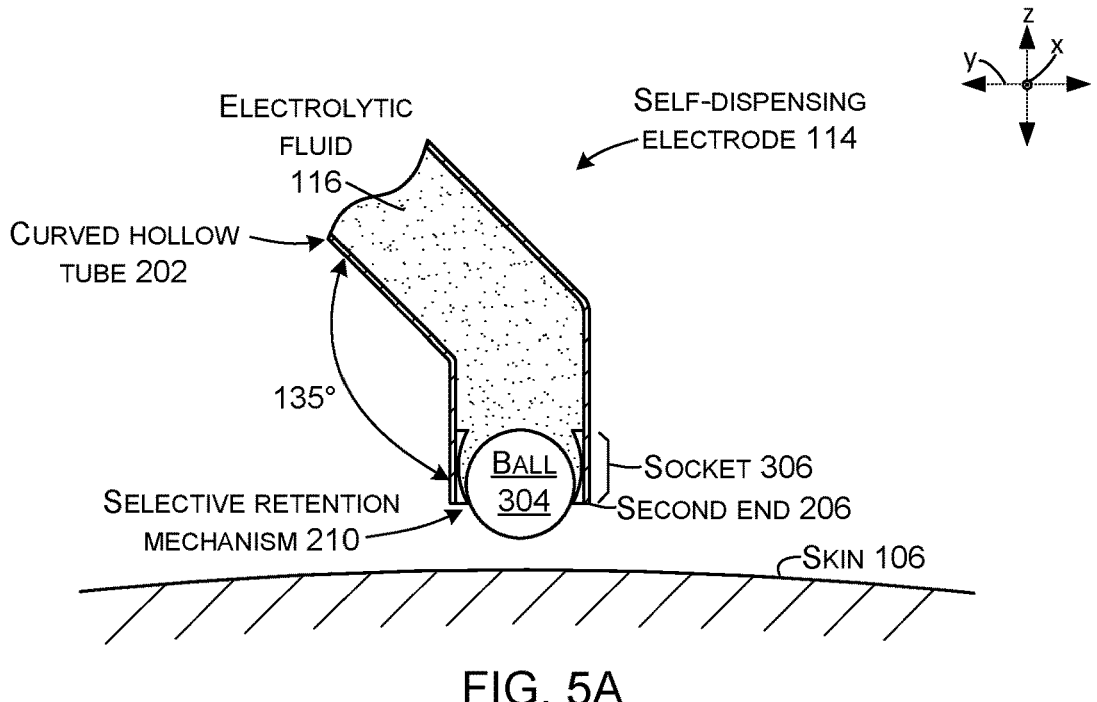
Figure 5B:
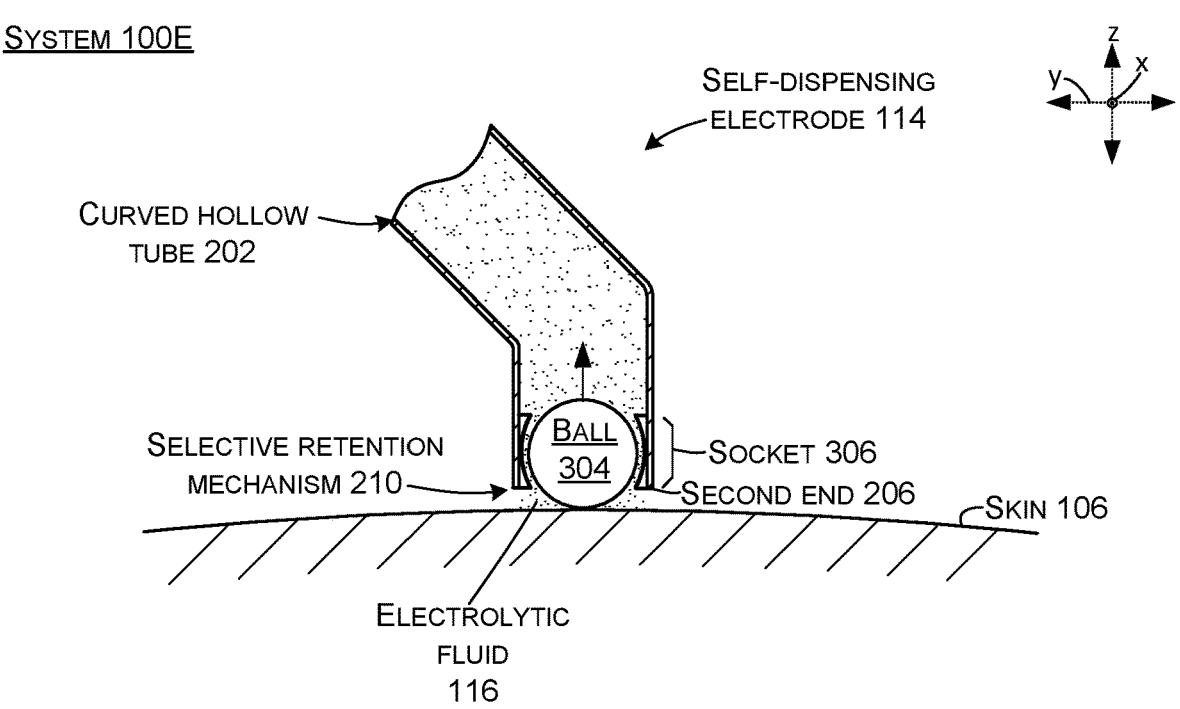

FIGS. 5A and 5B relate to system 100E and collectively show another example selective retention mechanism 210 employed on a self-dispensing electrode 114. FIG. 5A shows a non-dispensing state and FIG. 5B shows a dispensing state. In this case, the second end 206 of the curved hollow tube 202 is bent 135 degrees relative to a remainder of the tube. Similar to the implementation of FIGS. 4A and 4B, the ball 304 is captured in socket 306. The ball 304 blocks flow of electrolytic fluid 116 from the self-dispensing electrode 114 unless acted upon by contact with the user.

FIG. 5B shows contact between the self-dispensing electrode 114 and the user's skin 106 creating an upward force on the ball 304 that moves the ball linearly within the socket 306 and allows electrolytic fluid 116 to flow past the ball and onto the user's skin 106.

Ball 304 is captured in socket 306. When viewed along the z reference axis, the socket 306 has upper and lower diameters that are smaller than a diameter of the ball. Interposed between these upper and lower diameters is a region that has a diameter that is wider than the diameter of the ball. Thus, the ball 304 has a defined or limited range of movement between the upper and lower diameters of the socket, but the ball cannot pass out of the socket in the +z reference direction or the −z reference direction.

Figure 6A:
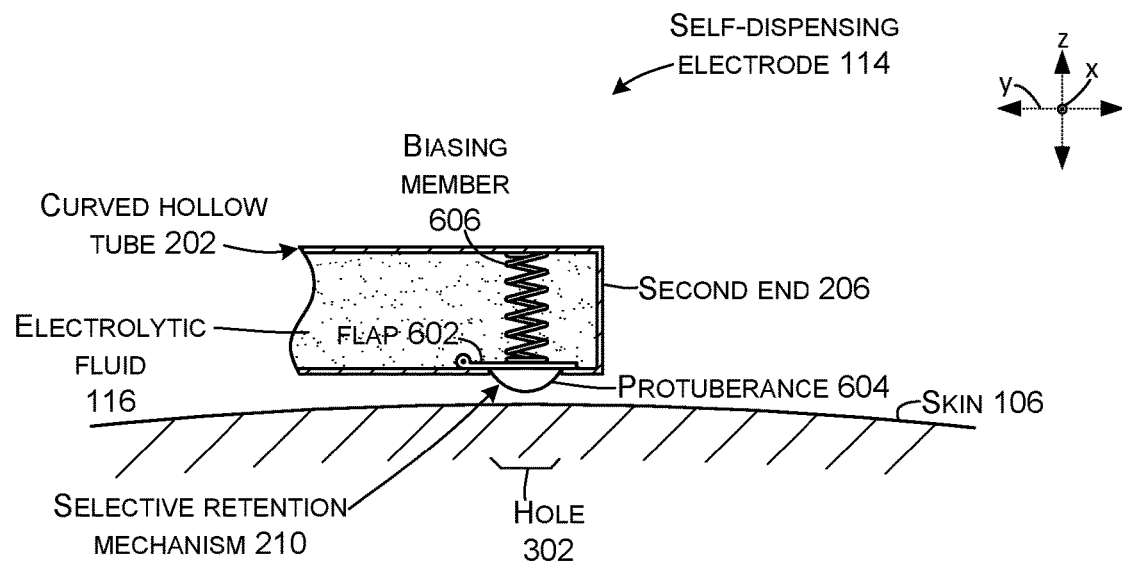
Figure 6B:
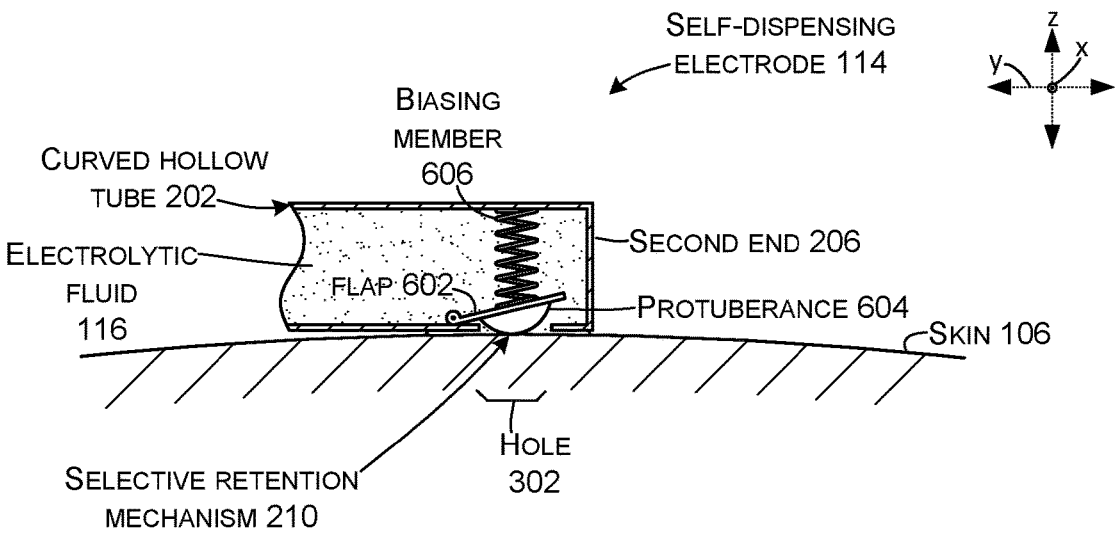

FIGS. 6A and 6B relate to system 100F and collectively show another example selective retention mechanism 210 employed on a self-dispensing electrode 114. In this case, the selective retention mechanism 210 includes a (hinged) flap 602 positioned over a hole 302 proximate to the second end 206 of the curved hollow tube 202. A protuberance 604 on the flap 602 extends through the hole 302. A biasing member 606, such as a spring, biases the flap 602 (e.g., biased flap) toward a closed orientation as shown in FIG. 6A. In this non-dispensing state shown in FIG. 6A, electrolytic fluid 116 is retained in the curved hollow tube 202.

FIG. 6B shows the self-dispensing electrode 114 moved toward the user's skin. Upward force/pressure from the skin on the protuberance 604 overcomes the downward bias on the flap 602 from the biasing member 606 and tilts the flap 602 to transition to a dispensing state. Tilting the flap 602 allows electrolytic fluid 116 to flow past the flap 602 and out the hole 302. When the self-dispensing electrode 114 is separated from the user, the biasing member 606 forces the flap 602 back down against the curved hollow tube 202 to seal the hole 302 and block flow of the electrolytic fluid 116.

FIGS. 7A and 7B relate to system 100G and collectively show another example selective retention mechanism 210 employed on a self-dispensing electrode 114. FIG. 7A shows a non-dispensing state and FIG. 7B shows a dispensing state. In this case, the selective retention mechanism 210 entails a bundle 702 of elements 704 that are retained in a hole in the curved hollow tube 202. Individual elements 704 of the bundle 702 can entail flexible filaments, strands, fibers, or bristles, among others. The elements 704 can be natural or synthetic materials, such as hairs, plant fibers, or polymer strands, among others.

As shown in FIG. 7A, the elements 704 are arranged generally parallel along the z reference axis. At this point, adjacent elements are parallel and touching along a majority of their length. The parallel nature blocks electrolytic fluid 116 from passing along the elements and out the hole.

FIG. 7B shows the self-dispensing electrode 114 against the user's skin 106. The user's skin 106 is imparting an upward force on the bottom of the bundle 702. The force is bending the elements 704 of the bundle 702. The bending causes the alignment of the elements 704 to decrease compared to FIG. 7A. Stated another way, the contact force from the skin 106 causes the degree of parallelism of the elements to decrease. The decreased alignment allows electrolytic fluid 116 to pass between the elements 704 of the bundle 702 and onto the user's skin. When the self-dispensing electrode 114 is moved away from the user's skin (e.g., pressure on the bundle ceases), the elements 704 of the bundle 702 will return to their aligned parallel orientation and block further electrolytic fluid 116 flow.

Figure 8A:
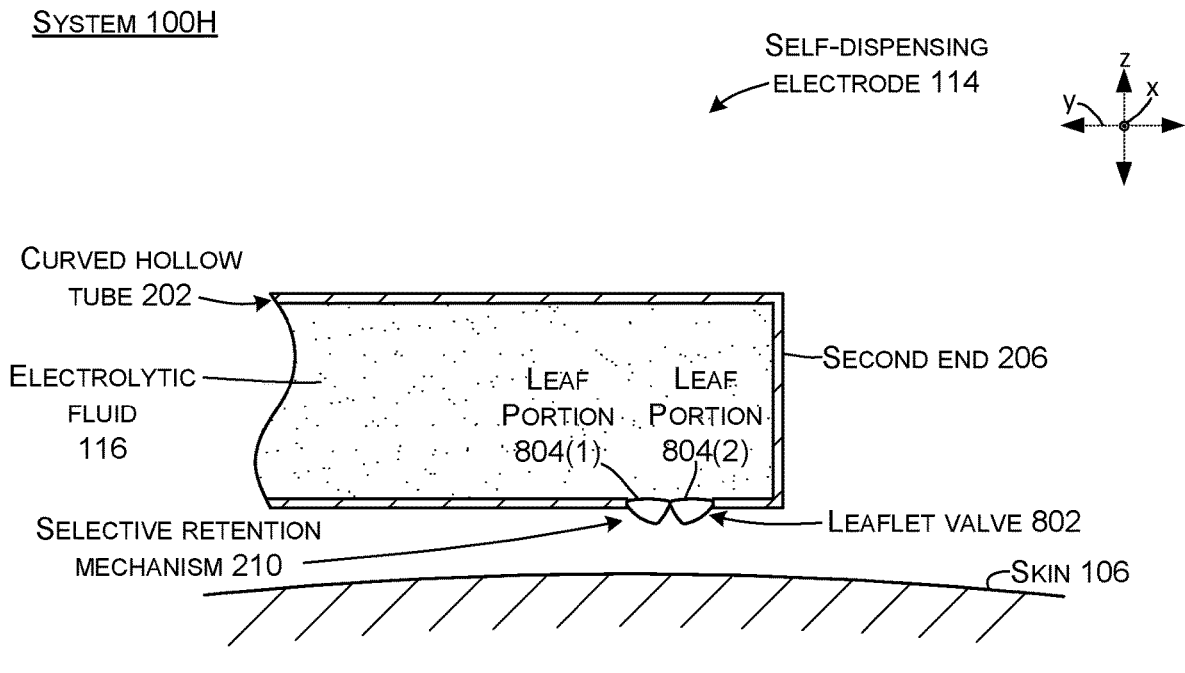
Figure 8B:
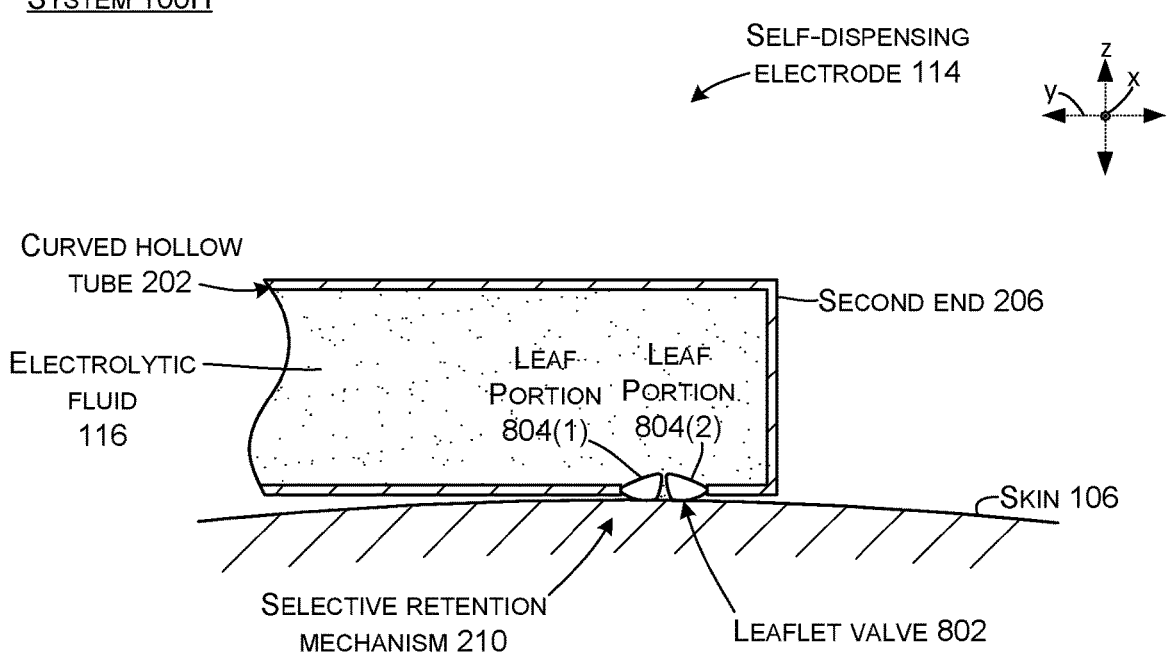

FIGS. 8A and 8B relate to system 100H and collectively show another example selective retention mechanism 210 employed on a self-dispensing electrode 114. FIG. 8A shows a non-dispensing state and FIG. 8B shows a dispensing state. In this implementation, the selective retention mechanism 210 entails a leaflet type valve 802. The leaflet valve includes opposing leaf portions 804. This implementation employs two leaf portions 804(1) and 804(2), but other implementations can employ more leaf portions, such as three or four leaf portions.

FIG. 8A shows the selective retention mechanism's leaf portions 804 in a resting or non-dispensing state. In this state, the leaf portions 804 contact each other along their lengths and create a seal that blocks flow of electrolytic fluid 116 from the curved hollow tube 202.

FIG. 8B shows the second end 206 of the curved hollow tube against the user's skin 106. The leaf portions 804 are contacting the skin, which is creating an upward force or pressure on the leaf portions 804. The upward force on the leaf portions 804 can create discontinuities in the seal created between the leaf portions 804 when compared to the resting state. The discontinuities produce gaps between the leaf portions 804. The electrolytic fluid 116 can flow through the gaps and onto the user's skin to decrease resistance/impedance in the electrical path between the user and the self-dispensing electrode 114. When the self-dispensing electrode 114 is moved away from the user, the leaf portions 804 return to the non-dispensing state of FIG. 8A and stop the flow of electrolytic fluid 116.

The present concepts can be adapted to many angles of approach between the curved hollow tube 202 and the skin 106. Illustrated examples include implementations where the selective retention mechanism is positioned on a portion of the hollow tube 202 that is approaching the skin 106 at a very small angle (e.g., parallel or close to parallel to the skin) shown in FIGS. 2A-2B, 3A-3D, 6A-6B, 7A-7B, and 8A-8B, orthogonal as shown in FIGS. 4A and 4B, and oblique angles shown in FIGS. 5A and 5B. This design flexibility lends itself to various form-factors. Three additional self-dispensing form-factors are described below relative to FIGS. 9A-9B, 10A-10B, and 11.

Figure 9A:
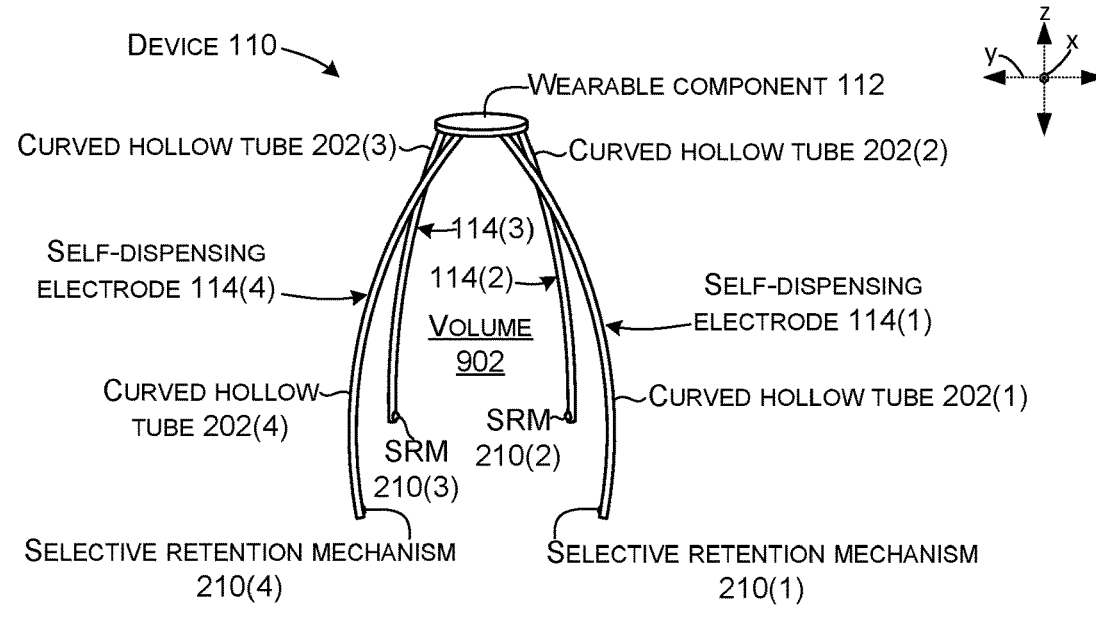
Figure 9B:
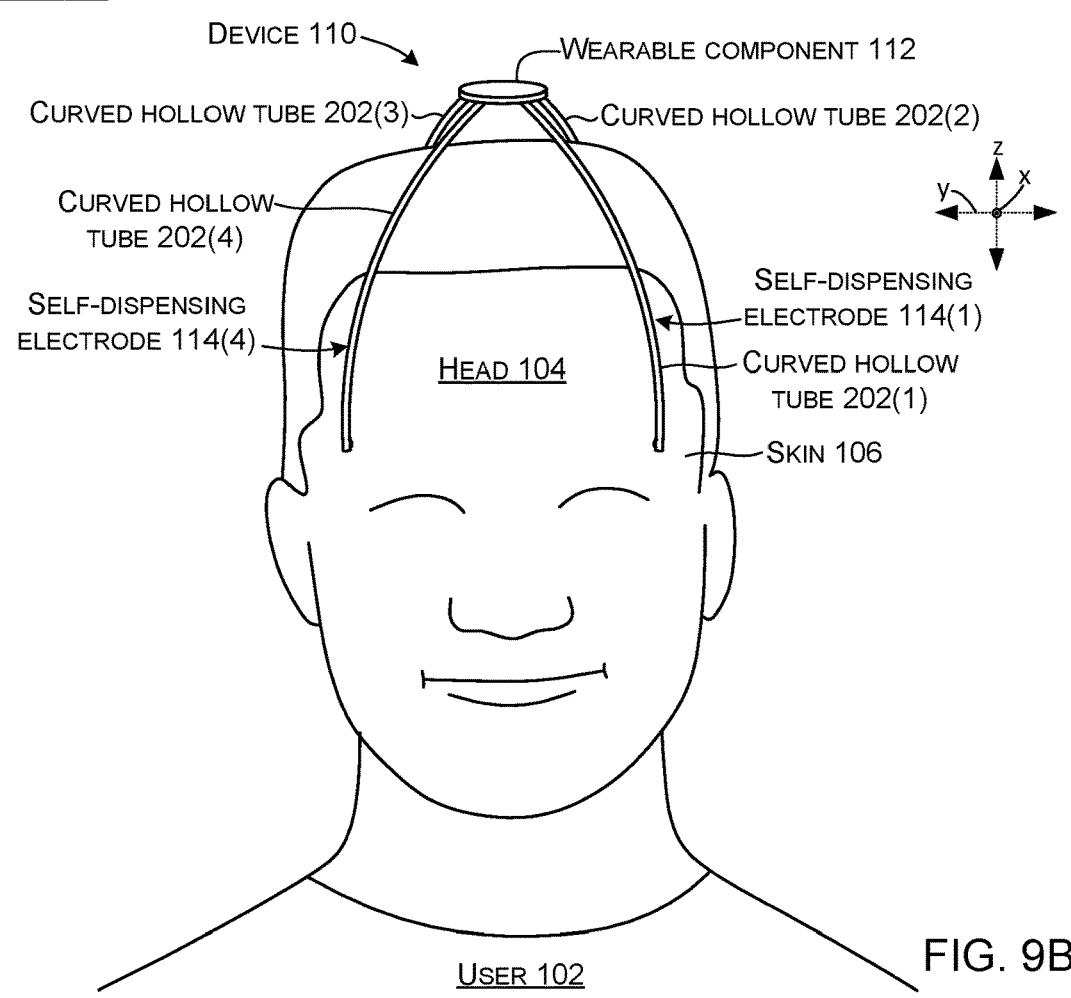

FIGS. 9A and 9B collectively show another system 100I. This system includes device 110 that is configured to be positioned on the user's head. FIG. 9A shows the device 110 in isolation in a non-dispensing state and FIG. 9B shows the device on the user's head in a dispensing state. The device 110 could be used in a free-standing form as shown in FIGS. 9A and 9B and/or could be integrated into another device, such as a garment in the form of a hat or hood.

In this case, as shown in FIG. 9A, the wearable component 112 serves as a hub for multiple radially arranged self-dispensing electrodes 114. The multiple self-dispensing electrodes 114 are arranged radially around the wearable component 112 and extend in the z reference direction and collectively define a resting volume 902. The resting volume 902 can be designed to be slightly smaller than a volume defined by the target body part of the user (in this case the user's head 104). The self-dispensing electrodes 114 include curved hollow tubes 202 that are elongate and are curved along their length (e.g., arc-shaped). Selective retention mechanisms 210 are positioned proximate to the second ends 206 of the curved hollow tubes 202. The selective retention mechanisms 210 are inwardly facing (e.g., facing toward the resting volume 902).

FIG. 9B shows the device 110 installed on the user's head, which as mentioned above is slightly larger in volume than the resting volume 902. The curved hollow tubes 202 are resilient and deform, such as bend or flex, to accommodate the increased volume. In this example, the bending of an individual curved hollow tube is along a plane that contains the z reference axis. This resilient bending ensures consistent contact of the selective retention mechanisms 210 against the skin of the user's head. Further, while not shown, the contact transitions the selective retention mechanisms 210 from a non-dispensing state to a dispensing state as described above relative to FIGS. 3A-3D, 4A-4B, 5A-5B, 6A-6B, 7A-7B, and 8A-8B. Positioning of the selective retention mechanisms 210 is not dependent upon the presence or absence of hair or other site preparation. Instead, the inward pressure of the curved hollow tubes 202 toward the head and the relatively small size and shape of the selective retention mechanisms 210 will contact the user's skin through hair or in the absence of hair. When the user removes the device from his/her head, the selective retention mechanisms 210 automatically return to the non-dispensing state and the curved hollow tubes 202 return to their original shape.

Figures 10A, 10B:
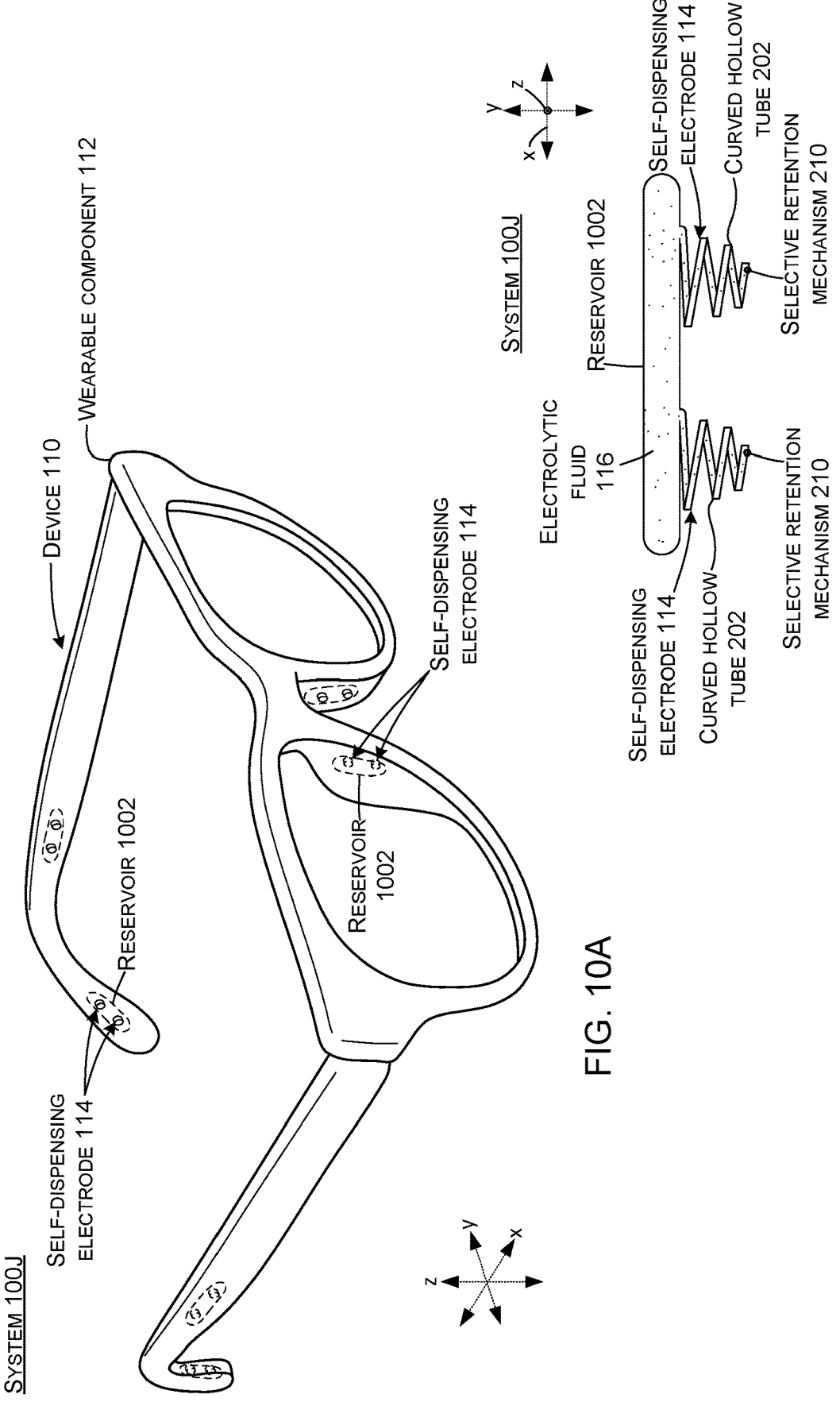

FIGS. 10A and 10B collectively show another system 100J. This system includes device 110 that is manifest as glasses or goggles. Self-dispensing electrodes 114 can be positioned on inwardly facing surfaces of the glasses to contact the user's skin. When the device 110 is positioned on the user's head, contact pressure causes the self-dispensing electrodes 114 to begin dispensing electrolytic fluid 116. In this implementation, the self-dispensing electrodes 114 may be relatively short in the direction toward the user, such as less than 0.5 cm (e.g., in the y reference direction of FIG. 10B). This relatively small dimension may reduce the storage capacity of electrolytic fluid 116 of the curved hollow tube 202. Reservoirs 1002 may be coupled to the curved hollow tubes 202 to increase the storage capacity. Note that not all self-dispensing electrodes 114 and reservoirs 1002 are labeled on the drawing page to reduce clutter.

In this case, two adjacent curved hollow tubes 202 share a common reservoir 1002. Other configurations can have a one-to-one ratio between curved hollow tubes 202 and reservoirs 1002. Other configurations may employ a many to one ratio. The curved hollow tubes 202 are fluidly coupled to the reservoir 1002. Electrolytic fluid 116 from the reservoir 1002 can replenish electrolytic fluid 116 dispensed from the curved hollow tubes 202 through the selective retention mechanism 210. This replenishment can allow the device 110 to function through multiple different sensing sessions.

Figure 11:
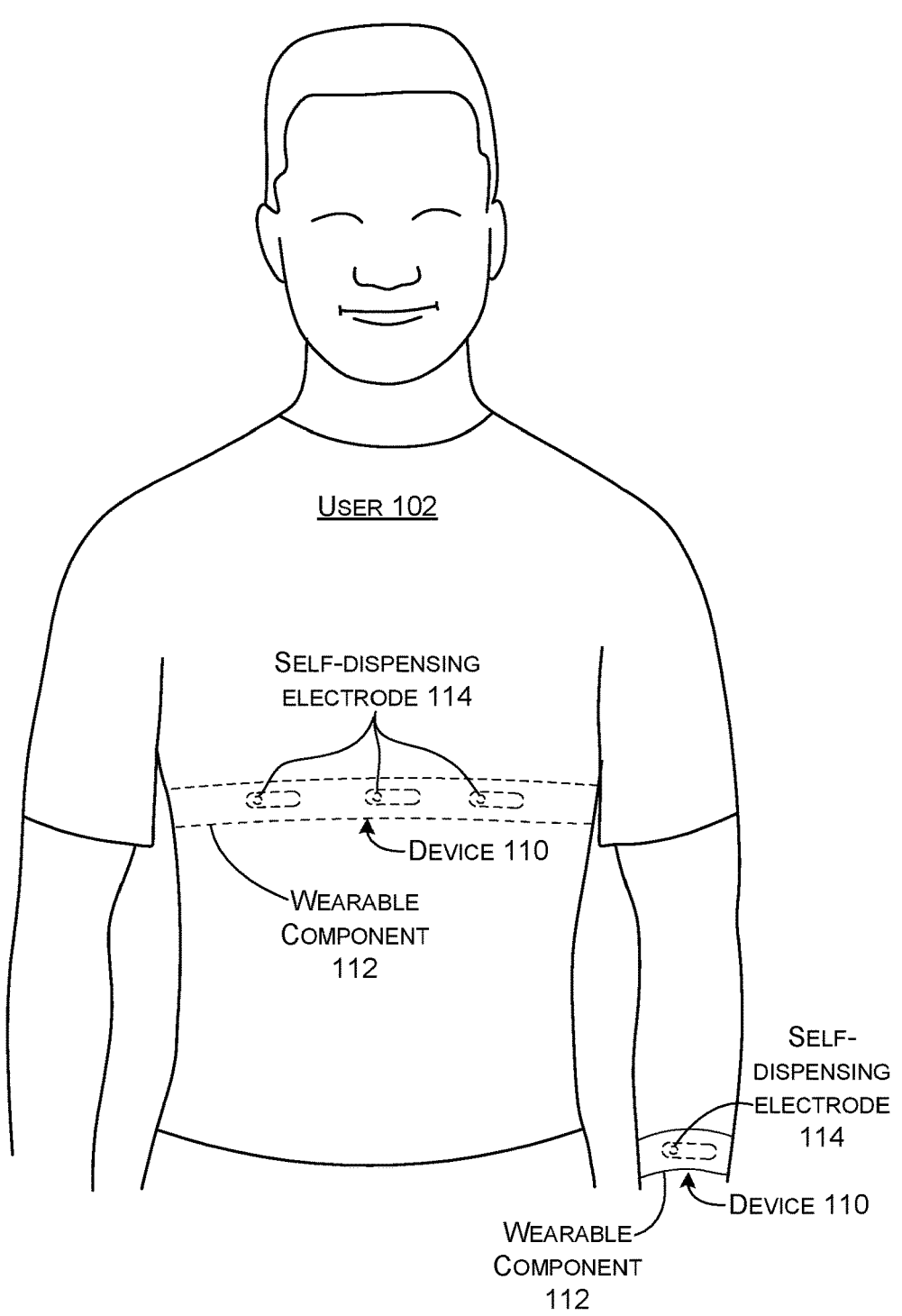

FIG. 11 shows another system 100K. This system includes device 110, such as an elastic belt positioned on the user's thorax and device 110, such as watch positioned on the user's wrist. Inwardly facing self-dispensing electrodes 114 can contact the user's skin in these regions to sense biological signals. Multiple example self-dispensing electrodes 114 are described above relative to FIGS. 2A-8B and those aspects are not re-introduced here for sake of brevity. Of note, the self-dispensing electrodes 114 will automatically dispense electrolytic fluid when the device is positioned on the user. The electrolytic fluid is dispensed from and thus is inherently aligned with the self-dispensing electrodes 114 to facilitate high quality sensing of the biological signals. The dispensing will automatically cease when the device is removed and will start again when the device is re-applied.

The concepts described above provide multiple technical advantages. First, the electrolytic fluid, such as chloride gel, stays in the curved hollow tube so it won't contact (e.g., be wasted in) the hair. Second, the curved, such as spiral shaped, hollow tube has a larger volume to store electrolytic fluid compared to straight tubes. Third, the curved hollow tube can serve as a cushion to counter the pressure when it contacts the skin, such as the scalp. Fourth, if unforeseen (e.g., unintended) pressure were applied on the electrodes the curved hollow tube will collapse or bend out of the way and it saves the risk of penetrating the scalp. Fifth, this approach saves preparation time, allows the user to put the electrodes on themselves, without technicians' assistance and simplifies the entire gelling process.

The present concepts provide technical solutions for the technical problems of applying conductive gel for electrodes. Any project or product with components using biological signals (electroencephalogram (EEG), electrocardiogram (ECG), electro potential difference of muscle cells (EMG), etc.) can benefit from the advantages offered by the present technical solutions. Brain-Computer Interfaces (BCI) are at a tipping point, and in the foreseeable future BCI will likely appear in commercial devices and impact productivity and entertainment scenarios. The present concepts eliminate obstacles to this adoption by providing self-dispensing electrodes that include curved hollow tubes filled with electrolytic fluid. These implementations allow the user to easily place the sensing device on their body without help or training and to remove it and replace as conveniently as possible. All of this convenience is accompanied by high performance because the automatically dispensed electrolytic fluid that decreases impedance is inherently in the correct location (e.g., aligned with the electrode) because it is dispensed from the electrode.

The present concepts provide technical solutions to automatic electrolytic fluid dispensing proximate to the tip of an electrode on the user's skin to improve signal reception by the electrode. The technical solution involves a curved hollow electrode that can store the electrolytic fluid. The curved hollow electrode can include a selective retention mechanism that dispenses the electrolytic fluid when contacting the user's skin and stops dispensing when the selective retention mechanism is removed from the user's skin. The technical solution provides several technical advantages. These technical advantages include the curved hollow tube having a greater length than a straight hollow tube to increase storage capacity. The curved hollow tube is resilient and flexes (e.g., compresses and extends while contacting the user's skin) to provide consistent contact with the skin even when the user moves. The resilient nature of the curved hollow tube eliminates the possibility of a 'spear affect' that could pierce the user's skin. Instead, if an unintentionally large force is imparted on the curved hollow tube, the curved hollow tube will collapse/bend and spread the force over a large area of the curved hollow tube as seen in FIG. 2B.

Various methods of manufacture, assembly, and/or use for self-dispensing electrodes are contemplated beyond those shown above relative to FIGS. 1A-11.

Although techniques, methods, devices, systems, etc., pertaining to self-dispensing electrodes are described in language specific to structural features and/or methodological acts, it is to be understood that the subject matter defined in the appended claims is not limited to the specific features or acts described. Rather, the specific features and acts are disclosed as example forms of implementing the claimed methods, devices, systems, etc.

Various examples are described above. Additional examples are described below. One example includes a wearable component configured to be positioned relative to a body part of a user and an electrode associated with the wearable component and configured to engage the user's body part, the electrode comprising a curved hollow tube configured to retain a flowable conductive material unless a force is exerted on the electrode toward the wearable component.

Another example can include any of the above and/or below examples where the wearable component comprises a hat, a helmet, a hood, a visor, glasses, goggles, a belt, or a watch.

Another example can include any of the above and/or below examples where the electrode is secured to the wearable component and extends toward the body part.

Another example can include any of the above and/or below examples where the curved hollow tube is elongate and a first end of the curved hollow tube proximate to the wearable component is connectable to a conductive wire and a second opposite end of the curved hollow tube that is distal from the wearable component comprises a selective retention mechanism that is configured to control the flowable conductive material.

Another example can include any of the above and/or below examples where the selective retention mechanism comprises a ball and socket.

Another example can include any of the above and/or below examples where the selective retention mechanism comprises a biased flap.

Another example can include any of the above and/or below examples where the selective retention mechanism comprises a bundle of fibers.

Another example can include any of the above and/or below examples where the selective retention mechanism comprises a leaflet valve.

Another example can include any of the above and/or below examples where the selective retention mechanism is positioned along a length of the curved hollow tube or wherein the selective retention mechanism is positioned at the second opposite end.

Another example includes an electrode comprising a curved hollow tube configured to hold a flowable conductive material and a selective retention mechanism positioned on the curved hollow tube and configured to retain the flowable conductive material in the curved hollow tube unless a force is imparted on the curved hollow tube.

Another example can include any of the above and/or below examples where the curved hollow tube is arc shaped or wherein the curved hollow tube is spiral shaped.

Another example can include any of the above and/or below examples where the flowable conductive material comprises an electrolytic fluid.

Another example can include any of the above and/or below examples where the curved hollow tube comprises an electrically insulative resilient material.

Another example can include any of the above and/or below examples where the curved hollow tube comprises a resilient material and where the force changes a state of the selective retention mechanism from a first state to a second state and changes the resilient material from a first shape to a second shape, and upon removal of the force, the selective retention mechanism returns to the first state and the resilient material returns to the first shape.

Another example can include any of the above and/or below examples where the curved hollow tube further comprises a port configured to allow the curved hollow tube to be refilled with additional flowable conductive material.

Another example can include any of the above and/or below examples where the selective retention mechanism comprises a ball and socket, a biased flap, a bundle of fibers, or a leaflet valve.

Another example includes a device comprising a wearable component configured to be positioned relative to a body part of a user and multiple deformable electrodes associated with the wearable component and individual deformable electrodes are configured to deform and release a flowable conductive material where or when subjected to a compressive force.

Another example can include any of the above and/or below examples where the individual deformable electrodes are configured to deform toward the wearable component when subjected to the compressive force.

Another example can include any of the above and/or below examples where the individual deformable electrodes are configured to deform along a line or wherein the individual deformable electrodes are configured to deform along a plane.

Another example can include any of the above and/or below examples where the individual deformable electrodes are configured to stop releasing the flowable conductive material when the compressive force is removed.

The invention claimed is:

1. A device, comprising:
   a wearable component configured to be positioned relative to a body part of a user; and,
   an electrode associated with the wearable component and configured to engage the user's body part, the electrode comprising a curved hollow tube configured to retain a flowable conductive material unless a compressive force is exerted on the electrode by the body part of the user that both compresses a length of the electrode and releases the flowable conductive material until the compressive force is removed.

2. The device of claim 1, wherein the wearable component comprises a hat, a helmet, a hood, a visor, glasses, goggles, a belt, or a watch.

3. The device of claim 1, wherein the electrode is secured to the wearable component and extends toward the body part.

4. The device of claim 3, wherein the curved hollow tube is elongate and a first end of the curved hollow tube proximate to the wearable component is connectable to a conductive wire and a second opposite end of the curved hollow tube that is distal from the wearable component comprises a selective retention mechanism that is configured to control the flowable conductive material.

5. The device of claim 4, wherein the selective retention mechanism comprises a ball and socket.

6. The device of claim 4, wherein the selective retention mechanism comprises a biased flap.

7. The device of claim 4, wherein the selective retention mechanism comprises a bundle of fibers.

8. The device of claim 4, wherein the selective retention mechanism comprises a leaflet valve.

9. The device of claim 4, wherein the selective retention mechanism is positioned along a curved surface of the curved hollow tube or wherein the selective retention mechanism is positioned at the second opposite end.

10. An electrode, comprising:
    a curved hollow tube configured to hold a flowable conductive material; and,
    a selective retention mechanism positioned on the curved hollow tube and configured to retain the flowable conductive material in the curved hollow tube unless a compressive force is imparted on the curved hollow tube that temporarily decreases a length of the curved hollow tube.

11. The electrode of claim 10, wherein the curved hollow tube is arc shaped or wherein the curved hollow tube is spiral shaped.

12. The electrode of claim 10, wherein the flowable conductive material comprises an electrolytic fluid.

13. The electrode of claim 10, wherein the curved hollow tube comprises an electrically insulative resilient material.

14. The electrode of claim 10, wherein the curved hollow tube comprises a resilient material and where the compressive force changes a state of the selective retention mechanism from a first state to a second state and changes the resilient material from a first shape to a second shape, and upon removal of the compressive force, the selective retention mechanism returns to the first state and the resilient material returns to the first shape.

15. The electrode of claim 10, wherein the curved hollow tube further comprises a port configured to allow the curved hollow tube to be refilled with additional flowable conductive material.

16. The electrode of claim 10, wherein the selective retention mechanism comprises a ball and socket, a biased flap, a bundle of fibers, or a leaflet valve.

17. A device, comprising:

a wearable component configured to be positioned relative to a body part of a user; and, multiple deformable electrodes associated with the wearable component and individual deformable electrodes are configured to have a resting length and a shorter compressed length when exposed to a compressive force and to release a flowable conductive material when subjected to the compressive force.

18. The device of claim 17, wherein the individual deformable electrodes are configured to deform toward the wearable component when subjected to the compressive force.

19. The device of claim 18, wherein the individual deformable electrodes are configured to deform along a line or wherein the individual deformable electrodes are configured to deform along a plane.

20. The device of claim 17, wherein the individual deformable electrodes are configured to stop releasing the flowable conductive material when the compressive force is removed.

* * * * *